United States Patent
Sheldrick et al.

(10) Patent No.: US 11,443,427 B2
(45) Date of Patent: Sep. 13, 2022

(54) MRI POST-PROCESSING SYSTEMS AND METHODS

(71) Applicant: MErunova Pty Ltd, Kogarah (AU)

(72) Inventors: Kyle Sheldrick, Bexley (AU); Ashish Diwan, Sydney (AU)

(73) Assignee: MERUNOVA PTY LTD., Kogarah (AU)

(*) Notice: Subject to any disclaimer, the term of this patent is extended or adjusted under 35 U.S.C. 154(b) by 0 days.

(21) Appl. No.: 17/455,677

(22) Filed: Nov. 19, 2021

(65) Prior Publication Data
US 2022/0076413 A1 Mar. 10, 2022

Related U.S. Application Data

(63) Continuation of application No. PCT/IB2020/055204, filed on Jun. 2, 2020.
(Continued)

(51) Int. Cl.
*G06T 7/00* (2017.01)
*G06T 7/62* (2017.01)
(Continued)

(52) U.S. Cl.
CPC .......... *G06T 7/0012* (2013.01); *A61B 5/004* (2013.01); *G06T 7/11* (2017.01); *G06T 7/62* (2017.01);
(Continued)

(58) Field of Classification Search
CPC . G06T 7/0012; G06T 7/11; G06T 7/62; G06T 2207/10088; G06T 2207/30012;
(Continued)

(56) References Cited

U.S. PATENT DOCUMENTS

| 6,529,763 B1 | 3/2003 | Cohen et al. |
| 9,808,177 B2 | 11/2017 | Claude et al. |

(Continued)

FOREIGN PATENT DOCUMENTS

| WO | 2013082207 A | 6/2013 |
| WO | 2019089998 A | 5/2019 |

OTHER PUBLICATIONS

Michopoulou et al. 2011 Acta Radiologica 52:91-98 (Year: 2011).*
(Continued)

*Primary Examiner* — Colin T. Sakamoto
*Assistant Examiner* — Patrick M Mehl
(74) *Attorney, Agent, or Firm* — Law Office of Andrei D Popovici, PC

(57) ABSTRACT

In some embodiments, spinal disc degeneracy is diagnosed according to a decay variance map generated by determining a variance in T2 decay over time within each pixel or pixel subset of an MRI image. A region of interest may be defined as including nucleus pulposus (NP) and annulus fibrosus (AF) areas, and excluding cartilaginous endplate (EP) areas of a disc. A decay variance for a pixel or groups of pixels is calculated by determining ratios between consecutive intensity values of the T2 signal, determining differences between consecutive ratios, and summing the absolute values of the determined differences. Decay variance mapping may be used to diagnose degeneracy in other tissues, such as in joints.

24 Claims, 8 Drawing Sheets

| Histological Grade | REPRESENATIVE DECAY VARIANCE IMAGE | Sample size (n) | T2 Score | Quantitative T2 Score | Decay Variance Score |
|---|---|---|---|---|---|
| 4 | | 24 | 0.59 (±0.08) | 0.28 (±0.13) | 0.49 (±0.07) |
| 5-11 | | 24 | 0.64 (±0.08) | 0.43 (±0.16) | 0.62 (±0.07) |
| 12 | | 27 | 0.65 (±0.11) | 0.43 (±0.16) | 0.71 (±0.07) |

Related U.S. Application Data

(60) Provisional application No. 62/856,201, filed on Jun. 3, 2019.

(51) Int. Cl.
*G06T 7/11* (2017.01)
*A61B 5/00* (2006.01)

(52) U.S. Cl.
CPC ............... *G06T 2207/10088* (2013.01); *G06T 2207/30012* (2013.01)

(58) Field of Classification Search
CPC ..... A61B 5/004; A61B 5/4504; A61B 5/4528; A61B 5/4538; A61B 2018/00339; A61F 2008/444
See application file for complete search history.

(56) References Cited

U.S. PATENT DOCUMENTS

| | | | |
|---|---|---|---|
| 10,045,711 B2 | 8/2018 | Peacock et al. | |
| 10,285,622 B2 | 5/2019 | Peacock et al. | |
| 2013/0211238 A1* | 8/2013 | DeCharms | A61B 5/4824 600/407 |
| 2018/0049665 A1 | 2/2018 | Jeong et al. | |
| 2018/0088051 A1 | 3/2018 | Georgakoudi et al. | |
| 2018/0110459 A1 | 4/2018 | Nevo et al. | |

OTHER PUBLICATIONS

Milford et al. 2015 PLoS ONE 10:e0145255 13 pages (Year: 2015).*

G.B.D. 2016 D. and I.I. and P. Collaborators, "Global, regional, and national incidence, prevalence, and years lived with disability for 328 diseases and injuries for 195 countries, 1990-2016: a systematic analysis for the Global Burden of Disease Study 2016," Lancet (London, England). 390 (2017) 1211-1259. doi:10.1016/S0140-6736(17)32154-2. Sep. 16, 2017.

J.K. Freburger, G.M. Holmes, R.P. Agans, A.M. Jackman, J.D. Darter, A.S. Wallace, L.D. Castel, W.D. Kalsbeek, T.S. Carey, The rising prevalence of chronic low back pain, Arch. Intern. Med. 169 (2009) 251-258. doi:10.1001/archintemmed.2008.543. Feb. 9, 2009.

C.-J. Zheng, J. Chen, Disc degeneration implies low back pain, Theor. Biol. Med Model. 12 (2015) 24. doi:10.1186/s12976-015-0020-3. Nov. 9, 2015.

P.-P.A. Vergroesen, I. Kingma, K.S. Emanuel, R.J.W. Hoogendoom, T.J. Welting, B.J. van Royen, J.H. van Dieën, T. H. Smit, Mechanics and biology in intervertebral disc degeneration: a vicious circle, Osteoarthr. Cartil. 23 (2015) 1057-1070. doi:https://doi.org/10.1016/j.joca.2015.03.028. Jul. 2015.

S.A. Chung, A.Q. Wei, D.E. Connor, G.C. Webb, T. Molloy, M. Pajic, A.D. Diwan, Nucleus Pulposus Cellular Longevity by Telomerase Gene Therapy, Spine (Phila. Pa. 1976). 32 (2007). https://journals.lww.com/spinejournal/Fulltext/2007/05150/Nucleus_Pulposus_Cellular_Longevity_by_Telomerase.7.aspx. Jun. 2007.

S.R. Damle, B.A. Rawlins, O. Boachie-Adjei, R.G. Crystal, C. Hidaka, M.E. Cunningham, Lumbar Spine Intervertebral Disc Gene Delivery: A Pilot Study in Lewis Rats, HSS J. ®. 9 (2013) 36-41. doi:10.1007/s11420-012-9319-3. Jan. 8, 2013.

F.C. Bach, N. Willems, L.C. Penning, K. Ito, B.P. Meij, M.A Tryfonidou, Potential regenerative treatment strategies for intervertebral disc degeneration in dogs, BMC Vet. Res. 10 (2014) 3. doi:10.1186/1746-6148-10-3. Jan. 4, 2014.

S. Miyazaki, A.D. Diwan, K. Kato, K. Cheng, W.C. Bae, Y. Sun, J. Yamada, C. Muehleman, M.E. Lenz, N. Inoue, R.L. Sah, M. Kawakami, K. Masuda, ISSLS Prize in Basic Science 2018: Growth differentiation factor-6 attenuated pro-inflammatory molecular changes in the rabbit anular-puncture model and degenerated disc-induced pain generation in the rat xenograft radiculopathy model., Eur. Spine J. Off. Publ. Eur. Spine Soc. Eur. Spinal Deform. Soc. Eur. Sect. Cerv. Spine Res. Soc. 27 (2018) 739-751. doi:10.1007/s00586-018-5488-1. Feb. 19, 2018.

C.W.A. Pfirrmann, A. Metzdorf, M. Zanetti, J. Hodler, N. Boos, Magnetic Resonance Classification of Lumbar Intervertebral Disc Degeneration, Spine (Phila. Pa. 1976). 26 (2001). https://journals.lww.com/spinejournal/Fulltext/2001/09010/Magnetic_Resonance_Classification_of_Lumbar.11 aspx. Sep. 2001.

A.M. Ellingson, H. Mehta, D.W. Polly, J. Ellermann, D.J. Nuckley, Disc degeneration assessed by quantitative T2* (T2 star) correlated with functional lumbar mechanics, Spine (Phila. Pa. 1976). 38 (2013) E1533-E1540. doi:10.1097/BRS.0b013e3182a59453. Dec. 2013.

C.P.L. Paul, T.H. Smit, M. de Graaf, R.M. Holewijn, A. Bisschop, P.M. van de Ven, M.G. Mullender, M.N. Helder, G.J. Strijkers, Quantitative MRI in early intervertebral disc degeneration: T1rho correlates better than T2 and ADC with biomechanics, histology and matrix content, PLoS One. 13 (2018) e0191442. https://doi.org/10.1371/journal.pone.0191442. Jan. 30, 2018.

W. Chen, Errors in quantitative T1rho imaging and the correction methods, Quant. Imaging Med. Surg. 5 (2015) 583-591. doi:10.3978/j.issn.2223-4292.2015.08.05. Aug. 2015.

A.B. Rosenkrantz, M. Mendiratta-Lala, B.J. Bartholmai, D. Ganeshan, R.G. Abramson, K.R. Burton, J.-P.J. Yu, E.M. Scalzetti, T.E. Yankeelov, R.M. Subramaniam, L. Lenchik, Clinical utility of quantitative imaging, Acad. Radiol. 22(2015) 33-49. doi:10.1016/j.acra.2014.08.011. Jan. 2015.

C.T. Buckley, J.A. Hoyland, K. Fujii, A. Pandit, J.C. Iatridis, S. Grad, Critical aspects and challenges for intervertebral disc repair and regeneration—Harnessing advances in tissue engineering, JOR Spine. 1 (2018) e1029. doi:10.1002/isp2.1029. Jul. 11, 2018.

A.A. Thorpe, F.C. Bach, M.A. Tryfonidou, C.L. Le Maitre, F. Mwale, A.D. Diwan, K. Ito, Leaping the hurdles in developing regenerative treatments for the intervertebral disc from preclinical to clinical, JOR Spine. 1 (2018) e1027. doi:10.1002/jsp2.1027. Jul. 4, 2018.

H.-L. Margaret Cheng, N. Stikov, N.R. Ghugre, G.A. Wright, Practical medical applications of quantitative MR relaxometry, J. Magn. Reson. Imaging. 36 (2012) 805-824. doi:10.1002/jmri.23718. Sep. 14, 2012.

M.-V. Corniola, M.N. Stienen, H. Joswig, N.R. Smoll, K. Schaller, G. Hildebrandt, O.P. Gautschi, Correlation of pain, functional impairment, and health-related quality of life with radiological grading scales of lumbar degenerative disc disease., Acta Neurochir. (Wien). 158 (2016) 499-505. doi:10.1007/s00701-015-2700-5. Jan. 19, 2016.

N. Henschke, C.G. Maher, K.M. Refshauge, A. Das, J.H. McAuley, Low back pain research priorities: a survey of primary care practitioners., BMC Fam. Pract. 8 (2007) 40. doi:10.1186/1471-2296-8-40. Jul. 11, 2007.

The National Institute of Arthritis and Musculoskeletal and Skin Diseases (NIAMS), Long-Range Plan Fiscal Years 2015-2019 Turning Discovery Into Health, 2015. https://www.niams.nih.gov/sites/default/files/files/2015-2019-Long-Range-Plan-final_0.pdf. Jun. 24, 2014.

N. Owusu, Characterization of T1rho sensitivity to metabolite and temperature changes, University of Iowa, 2015. https://ir.uiowa.edu/etd/1889/. Aug. 2015.

Australian Patent Office, International Search Report and Written Opinion dated Aug. 18, 2020 for PCT International Application No. PCT/IB2020/055204, International Filing Date Jun. 2, 2020.

Australian Patent Office, International Preliminary Repod on Patentability dated Dec. 16, 2021 for PCT International Application No. PCT/IB2020/055204, International Filing Date Jun. 2, 2020.

Zhang, X. et al., "Improved Liver R2* Mapping by Averaging Decay Curves"—Scientific Reports, www.nature.com—Jul. 21, 2017.

European Patent Office (EPO), Extended European Search Report dated May 25, 2022 for European Patent Application No. 20818181.8, regional stage of PCT International Application No. PCT/IB2020/055204, International Filing Date Jun. 2, 2020.

(56) References Cited

OTHER PUBLICATIONS

Oakes et al., "MRI-Based Measurements of Aerosol Deposition in the Lung of Healthy and Elastase-Treated Rats," Journal of Applied Physiology 116(12):1561-1568, Jun. 2014.

* cited by examiner

| Histological Grade | REPRESENATIVE DECAY VARIANCE IMAGE | Sample size (n) | T2 Score | Quantitative T2 Score | Decay Variance Score |
|---|---|---|---|---|---|
| 4 | | 24 | 0.59 (±0.08) | 0.28 (±0.13) | 0.49 (±0.07) |
| 5-11 | | 24 | 0.64 (±0.08) | 0.43 (±0.16) | 0.62 (±0.07) |
| 12 | | 27 | 0.65 (±0.11) | 0.43 (±0.16) | 0.71 (±0.07) |

FIG. 7

MRI POST-PROCESSING SYSTEMS AND METHODS

RELATED APPLICATION DATA

This application is a (bypass) continuation of PCT International Patent Application No. PCT/IB2020/055204, filed Jun. 2, 2020, entitled "MRI Post-Processing Systems and Methods," which claims priority from U.S. Provisional Patent Application No. 62/856,201, filed Jun. 3, 2019, entitled "MRI Post-Processing Systems and Methods," both of which are herein incorporated by reference.

BACKGROUND

The invention relates to medical diagnostics using magnetic resonance imaging (MRI) data, and in particular to systems and methods for diagnosing tissue degeneration using MRI data.

Low back pain is a leading cause of years lived with disability (YLD) in both men and women worldwide, contributing approximately 57.6 million years to the total YLDs in 2016. In the United States of America, back pain is estimated to cost more than U$100 billion per year. The prevalence of chronic disabling back pain has tripled in 20 years by some measures.

A major cause of low back pain is the degeneration of the Intervertebral Disc (IVD). The IVD consists of three parts in one functional unit: a gelatinous center called the nucleus pulposus (NP), an outer fibrocartilaginous ring called the annulus fibrosus (AF), and top and bottom caps called the cartilaginous endplates (EPs). Degeneration of the IVD is a complex pathological process characterized by a loss of hydration, changes in cell populations, a decrease in protein concentrations and altered biomechanical properties.

Diagnosing tissue degeneration such as intervertebral disc degeneration or joint damage using MRI images can be challenging. Qualitative schemes used in clinical practice can correlate poorly with pain, and quantitative techniques have not entered widespread clinical use.

SUMMARY

According to one aspect, a method comprises employing a computer system including at least one hardware processor to: determine a signal decay variance for a pixel or pixel subset of a plurality of pixels of at least one magnetic resonance imaging (MRI) image of at least one region of interest of a subject, the signal decay variance representing a time-variance of a decay rate of an MRI signal characterizing the pixel or pixel subset; generate an MRI signal decay variance map of the at least one region of interest according to determined signal decay variances characterizing the at least one MRI image; and generate a tissue degeneration indicator for the subject according to the MRI signal decay variance map.

According to another aspect, a non-transitory computer readable medium encodes instructions which, when executed by a computer system, cause the computer system to: determine a signal decay variance for a pixel or pixel subset of a plurality of pixels of at least one magnetic resonance imaging (MRI) image of at least one region of interest of a subject, the signal decay variance representing a time-variance of a decay rate of an MRI signal characterizing the pixel or pixel subset; generate an MRI signal decay variance map of the at least one region of interest according to determined signal decay variances characterizing the at least one MRI image; and generate a tissue degeneration indicator for the subject according to the MRI signal decay variance map.

According to another aspect, a computer system comprises at least one processor programmed to: determine a signal decay variance for a pixel or pixel subset of a plurality of pixels of at least one magnetic resonance imaging (MRI) image of at least one region of interest of a subject, the signal decay variance representing a time-variance of a decay rate of an MRI signal characterizing the pixel or pixel subset; generate an MRI signal decay variance map of the at least one region of interest according to determined signal decay variances characterizing the at least one MRI image; and generate a tissue degeneration indicator for the subject according to the MRI signal decay variance map.

BRIEF DESCRIPTION OF THE DRAWINGS

The foregoing aspects and advantages of the present invention will become better understood upon reading the following detailed description and upon reference to the drawings where:

FIG. 7 shows exemplary average scores for segmented ROIs determined using three MRI post-processing techniques for different IVD grades, alongside representative decay variance maps, according to some embodiments of the present invention.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Pixels (picture elements) may be part of 2-D and/or 3-D images; pixels forming part of a 3-D array are sometimes also termed voxels. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass non-transitory media such as magnetic, optic, and semiconductor storage media (e.g. hard drives, optical disks, flash memory, DRAM), as well as communications links such as conductive cables and fiber optic links. According to some embodiments, the present invention provides, inter alia, computer systems comprising hardware (e.g. one or more processors) programmed to perform the methods described herein, as well as computer-readable media encoding instructions to perform the methods described herein.

Figure 1:
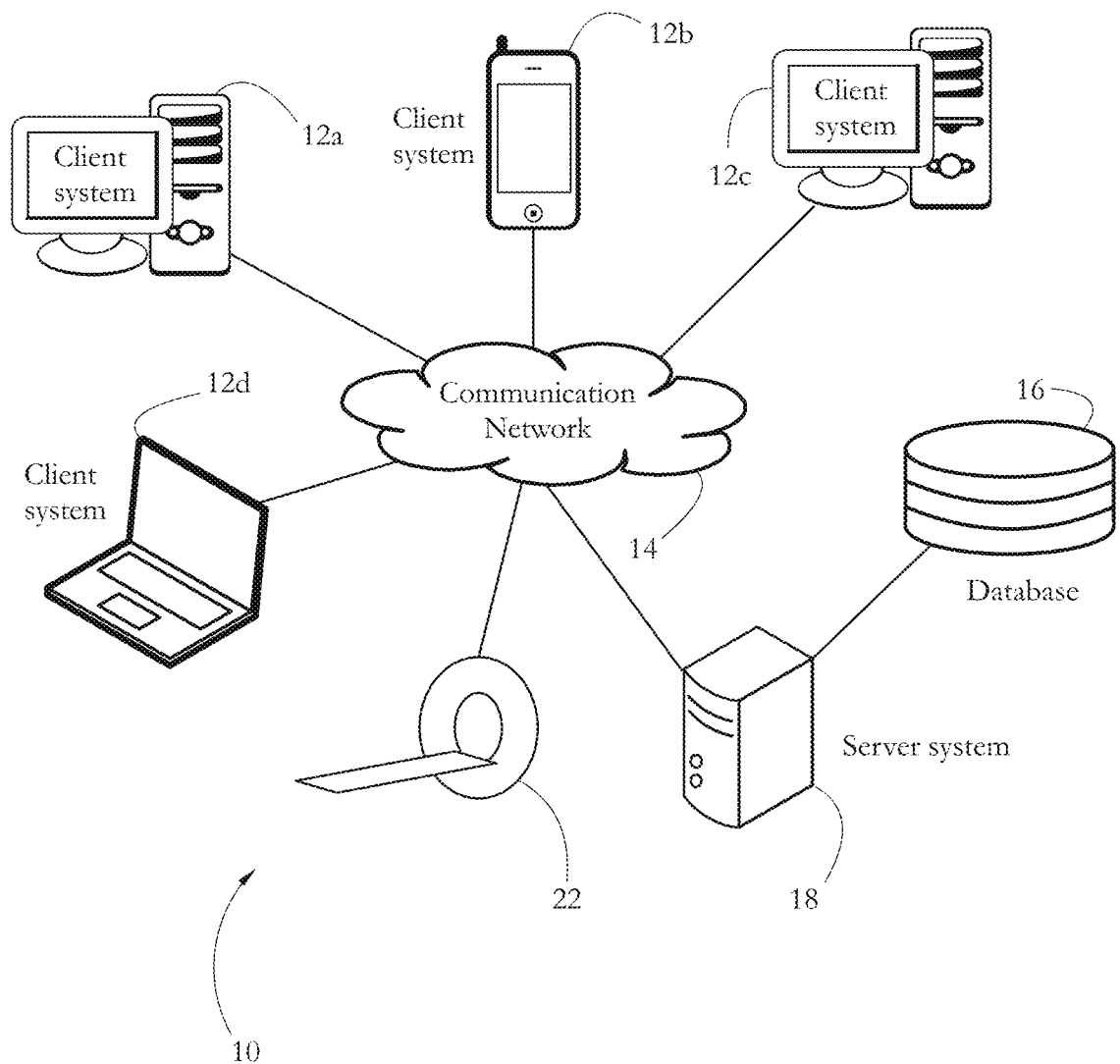
FIG. 1 shows an exemplary medical image analysis system according to some embodiments of the present invention.

FIG. 1 shows an exemplary medical image analysis system 10 according to some embodiments of the present invention. A plurality of client systems 12a-d may interact with a server system 18 over a communications network 14. Communications network 14 may include at least parts of a wide area network (a network including at least one router/OSI layer 4 device), and/or a local area network (a network including switches/OSI layer 2 devices). Server system 18 may connect to client systems 12a-d using one or more network protocols including TCP/IP, HTTP/HTTPS (Hypertext Transfer Protocol/Secure), and/or other protocols suitable for interchanging data between web services. Server system 18 may include one or more interconnected servers, and is connected to a database 16. Server system 18 may include servers hosted at different locations, and possibly owned by different entities. For example, server system 18 may include servers operated by medical image processing service provider, as well as servers operated by third party service providers (e.g. Amazon Web Services, or AWS). In some embodiments, different servers may be used to implement different parts of the functionality described below; for example, authentication and account management functions may be provided by one set of servers, while more computationally-intensive image processing functions may be provided by another, distinct set of servers of server system 18.

Exemplary client systems 12a-d include personal computer systems, mobile computing platforms (laptop computers, tablets, mobile telephones), entertainment devices (TVs, game consoles), augmented reality (AR) devices, virtual reality (VR) devices such as headsets and associated input devices, and/or other electronic devices comprising a processor, a memory, and a communication interface.

A magnetic resonance imaging (MRI) scanner 22 include magnets and associated circuitry and processors for generating sequences of MRI images of at least parts of subjects of interest. The subjects may be non-human mammalian subjects, and/or human patients in medical settings or other human subjects.

In some embodiments, the decay variance computation, display and subsequent use steps are performed by post-processing using client systems 12 and server system 18. In some embodiments, at least some of the decay variance determination and use steps described below may be performed by scanner 22.

Figure 2:
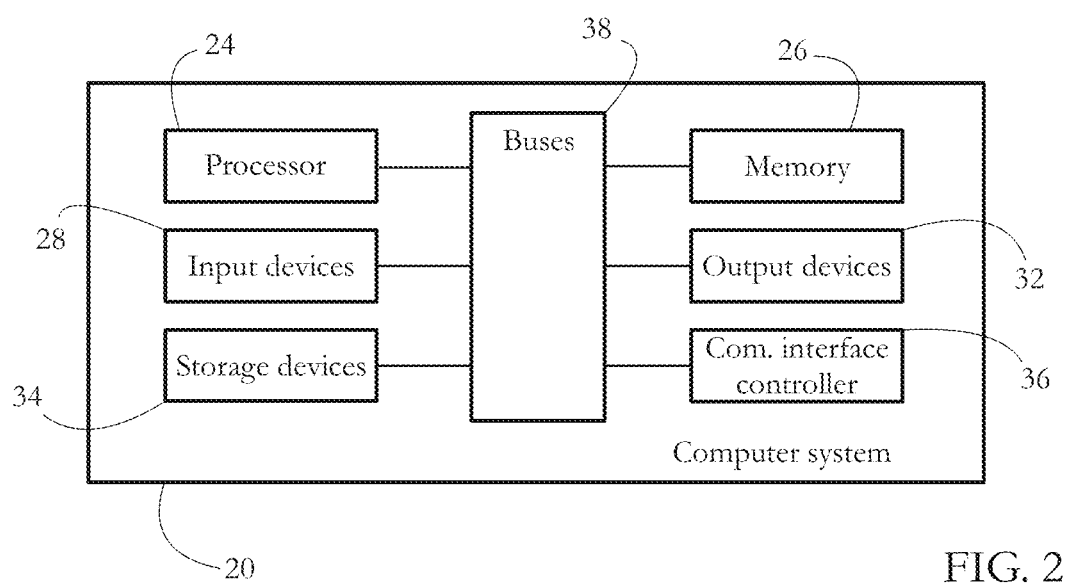
FIG. 2 shows an exemplary hardware configuration of a medical image data processing system according to some embodiments of the present invention.

FIG. 2 shows an exemplary hardware configuration of an exemplary computer system 20, which may represent a client system 12a-d and/or at least part of server system 18. Without loss of generality, the illustrated client system is a computer system. The hardware configuration of other client systems (e.g., mobile telephones, smartwatches) may differ somewhat from the one illustrated in FIG. 2. Computer system 20 comprises a set of physical devices, including a hardware processor 24 and a memory unit 26. Processor 24 comprises a physical device (e.g. a microprocessor, a multi-core integrated circuit formed on a semiconductor substrate, etc.) configured to execute computational and/or logical operations with a set of signals and/or data. In some embodiments, such operations are delivered to processor 24 in the form of a sequence of processor instructions (e.g. machine code or other type of encoding). Memory unit 26 may comprise volatile computer-readable media (e.g. DRAM, SRAM) storing instructions and/or data accessed or generated by processor 24.

Input devices 28 may include computer keyboards, mice, and microphones, among others, including the respective hardware interfaces and/or adapters allowing a user to introduce data and/or instructions into computer system 20. Output devices 32 may include display devices such as monitors and speakers among others, as well as hardware interfaces/adapters such as graphic cards, allowing computer system 20 to communicate data to a user. In some embodiments, input devices 28 and output devices 32 may share a common piece of hardware, as in the case of touch-screen devices. Storage devices 34 include computer-readable media enabling the non-volatile storage, reading, and writing of software instructions and/or data. Exemplary storage devices 34 include magnetic and optical disks and flash memory devices, as well as removable media such as CD and/or DVD disks and drives. A set of network adapters (communications interface controllers) 36 enables computer system 20 to connect to a computer network and/or to other devices/computer systems. A controller hub 38 represents the plurality of system, peripheral, and/or chipset buses, and/or all other circuitry enabling the communication between processor 24 and devices 26, 28, 32, 34, and 36. For instance, controller hub 38 may include a memory controller, an input/output (I/O) controller, and an interrupt controller, among others. In another example, controller hub 38 may comprise a northbridge connecting processor 24 to memory 26 and/or a southbridge connecting processor 24 to devices 28, 32, 34, and 36.

In some embodiments, server system 18 includes authentication and account management components configured to receive authentication data (e.g. username/password) and account management information (e.g. account ID, contact data, payment data, human and/or animal patient data, and other associated account information) from one or more client systems 12. Server system 18 further includes image management and processing components coupled to the authentication and account management components, and configured to receive patient images (e.g. MRI images) from client systems 12 and/or scanner 22, process the images as described herein, and transmit processed data (e.g. processed images, metadata, statistical information derived from the original and/or processed images, diagnostic data such as a tentative diagnosis, and other report results) to client systems 12. In some embodiments, account types may include patient (end-user) accounts, and medical service provider (e.g. radiology or other medical practice) accounts, which may be configured to transmit and/or receive data using client systems 12.

Figure 3:
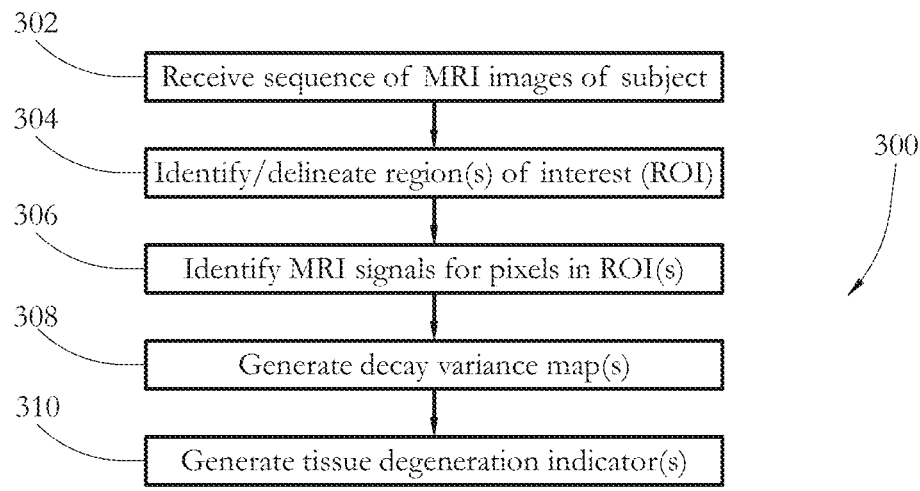
FIG. 3 shows a sequence of steps performed according to some embodiments of the present invention.

FIG. 3 shows a sequence of steps 300 performed according to some embodiments of the present invention. In a step 302, a sequence of MRI images including one or more areas of interest of a subject is received from an MRI scanner or storage. Exemplary areas of interest include at least part of the subject's spine, and/or a joint such as a knee, elbow, shoulder or hip joint. The MRI images may include a number of MRI signals known in the art, including without limitation T1 (spin-lattice) signals, T2 (spin-spin) signals, and variants of T1/T2 signals such as T1-rho and T2* signals.

In a step 304, one or more regions of interest (ROI) are identified/delineated in the MRI images. Delineating ROIs may be performed automatically via image recognition code, and/or by a human operator using a graphical user interface to label parts of the image (and thus associated pixels) as belonging to given ROIs. Exemplary ROIs may include regions of an intervertebral disc (IVD) such as nucleus pulposus (NP), annulus fibrosus (AF), and cartilaginous endplates (EP). Other ROIs may include different parts of a joint, such as parts defined by different tissue types (e.g. bone, cartilage, ligament).

In a step 306, MRI signals of interest characterizing pixels or groups of pixels within the ROIs are identified. Each MRI signal may include a sequence of intensity values defining one or more decay rates across the timespan of the signal. While the discussion below focuses on a per-pixel analysis method, the described analysis methods can also be performed at the level of image subareas formed by groups of pixels (e.g. 1×2, 2×2, or 2×2×2, pixels). A representative signal may be generated per image subarea, e.g. by summing or averaging, and the described decay variance computation can be performed for each representative signal. Such an approach may be computationally simpler and may yield higher signal-to-noise ratios, at the cost of loss of resolution. Loss of resolution may be acceptable in some circumstances, particularly when imaging relatively large areas of a subject.

In a step 308, a decay variance map for the ROI(s) is generated from the MRI signals as described in detail below. The decay variance map includes one or more decay variances computed for each pixel/subarea in the ROI(s).

In a step 310, one or more tissue degeneration indicators for the subject are generated using the decay variance map. The tissue degeneration indicators are indicative of representative decay variance values within one or more ROIs. Generating the tissue degeneration indicator may include summing determined decay variances over one or more ROI(s), averaging decay variances, otherwise determining a representative decay variance value/indicator, and/or normalizing the values to a given scale (e.g. 0 to 1, or 0 to 100). In some embodiments, the tissue degeneration indicator may be a numerical score, for example a score between 0 and 1, where a higher score indicates more advanced degeneration of the tissue. In some embodiments, the tissue degeneration indicator is an indicator of intervertebral disc degeneration. In some embodiments, the tissue degeneration indicator may characterize spinal cord injuries, and/or osteoarthritis of the knee, hip, or other joint, among others.

Generating a tissue degeneration indicator according to a decay variance map may be performed in different ways, and in particular may be performed according to adjusted rather than raw decay variances. In some embodiments, a raw decay variance for a ROI, generated as described below, may be converted to an adjusted decay variance representing a proportion of decay variance at a reference biological structure or substance (e.g. cerebrospinal fluid) in the same patient, or a proportion of the maximal decay variance observed in the patient, or a proportion of a value at a fixed percentile (e.g. 0.6 means 60% as much variance as the pixel that is at the $90^{th}$ centile for that patient). In some embodiments, raw decay variances may be converted to an ordinal (rank) score by reference to population data (e.g. a degeneration of a certain grade/rank would be based on an average decay variance within a corresponding range). In some embodiments, raw decay variances for a ROI may be converted to percentiles by reference to population data (e.g. 0.98 represents a disc that is more degenerate than 98% of the population).

In some embodiments, a decay variance value for a pixel/subarea is determined as described below. Consider an MRI signal for a pixel, the signal defined by a sequence of n signal intensity values, each corresponding to an echo time index i, $SI_i$=1, 2, . . . , n. A signal retention ratio (SR) is determined for the $(i+1)^{th}$ echo time, i=1, 2, . . . , n−1 as the ratio of consecutive single intensity values:

$$SR_{i+1} = \frac{SI_{i+1}}{SI_i} \tag{1}$$

A signal decay change (SDC) is determined for the $(i+2)^{th}$ echo time, i=1, 2, . . . , n−2, as the absolute value of the difference between consecutive signal retention ratios:

$$SDC_{i+2}=|SR_{i+2}-SR_{i+1}| \tag{2}$$

A decay variance value for a signal comprising n intensity value acquisitions is determined as the sum of signal decay changes over the timespan of the signal:

$$DV=\Sigma_{i=1}^{n-1}SDC_{i+2} \tag{3}$$

which may be rewritten in terms of signal retention ratios as $$DV=\Sigma_{i=1}^{n-2}|SR_{i+2}-SR_{i+i}| \tag{4}$$

and in terms of signal intensity values as $$DV = \sum_{i=1}^{n-2} \left| \frac{SI_{i+2}}{SI_{i+1}} - \frac{SI_{i+1}}{SI_i} \right| \tag{5}$$

In some embodiments, a normalization step is used to normalize data by signal intensity. Specifically, the determined decay variance for a pixel may be divided by the initial signal intensity for the pixel, to account for different signal-to-noise ratios of signals having different intensities. Some of the expected noise is fixed, i.e. not depending on signal intensity. Thus, data corresponding to lower signal intensities may exhibit artificially-high decay variance due to such noise. In some embodiments, T2 and decay variance were observed to show substantial correlation (e.g. r of about 0.11) in the absence of signal-intensity normalization, and substantially-lower correlation (e.g. r of less than 0.001) after signal-intensity normalization. A decay variance map generated using signal-intensity normalization is expected to more faithfully represent decay variance, rather than other variables such as T2.

Representing decay variances as differences in consecutive data point amplitude ratios, as described above, is relatively computationally-efficient. In some embodiments, decay variances may be represented by other second-derivative indicators generally denoting acceleration, or change-of-change, in signal amplitudes for a given pixel. In some embodiments, exemplary difference (subtraction) and/or ratio (division) operations used to perform comparisons may be replaced or supplemented by other comparison operations. Suitable comparison operations may include subtraction, division, determination whether a difference, ratio or other indicator exceeds a threshold, and/or other comparison operations. For example, indicators such as SR and SDC described above may be replaced with discrete levels that different computed values snap to.

In some embodiments, an average of decay rate ratios is generated over a signal time sequence for a given pixel, and then a sequence of comparison indicators (e.g. differences) is generated by comparing each ratio to the average, rather than the immediately-preceding ratio. Such an approach, which involves comparison to a decay rate average rather than preceding data, exhibits less variance and may be less sensitive to spurious variations in decay rate due to noise in the underlying data. Such an approach, however, was observed to perform less well than the consecutive-ratio comparison approach described above with reference to eqs. (1-5).

In some embodiments, an approach that is significantly more computationally intensive involves breaking down each time sequences into n-tuples (subsequences) shorter than the entire curve, curve-fitting over each subsequence, and comparing the decay rate of each subsequence to the immediately-preceding (and/or subsequent) one. Such subsequences may be constrained to extend over a millisecond (ms) scale or shorter. For example, a T2 sequence may be divided into triplets, a decay rate may be generated for each triplet by curve-fitting, and each pair of consecutive rates may be compared to each other (e.g. by subtraction, division, determination whether a difference or ratio exceeds a threshold, or other comparison operation) to generate a sequence of comparison indicators. Such an approach may be a factor of 1000× slower than the exemplary approach illustrated above with reference to eqs. (1-5). Data analysis for n-tuples larger than triplets may be even slower.

In some embodiments, pixel values over 85% may be deemed to be at unity. Such snapping-to-unity may be used to facilitate fair comparisons to conventional quantitative T2 analysis. Quantitative T2 analysis works out exponential decays, and may be sensitive to wild (and unrepresentative) outliers. In particular, for relatively-flat curves (long decays), noise can have large effects on measured decay rates. For example, for an analysis method measuring time-to-$\frac{2}{3}$-signal loss, noise can alter measured data by several orders of magnitude. Thus, snapping-to-unity may be employed as a fairness check for ensuring that conventional T2 analysis is fairly represented in comparisons.

In some embodiments, raw T2 data refers to unitless data (e.g. T2 value) corresponding to a given time point (e.g. at 100 ms). Raw T2 data may generally depend on the details of the particular MRI machine and/or practice, and may not be generally useful for comparison across medical practices. Raw T2 data may be useful for comparing different parts of the same image (e.g. one vertebral disc to another).

In some embodiments, signals other than T2 may be used to generate decay variance maps as described above. For example, T2* data correlates with corresponding T2 data, and is shorter by a given ratio. In some embodiments, T1-rho sequences may be used to generate decay variance maps as described herein.

Figure 4:
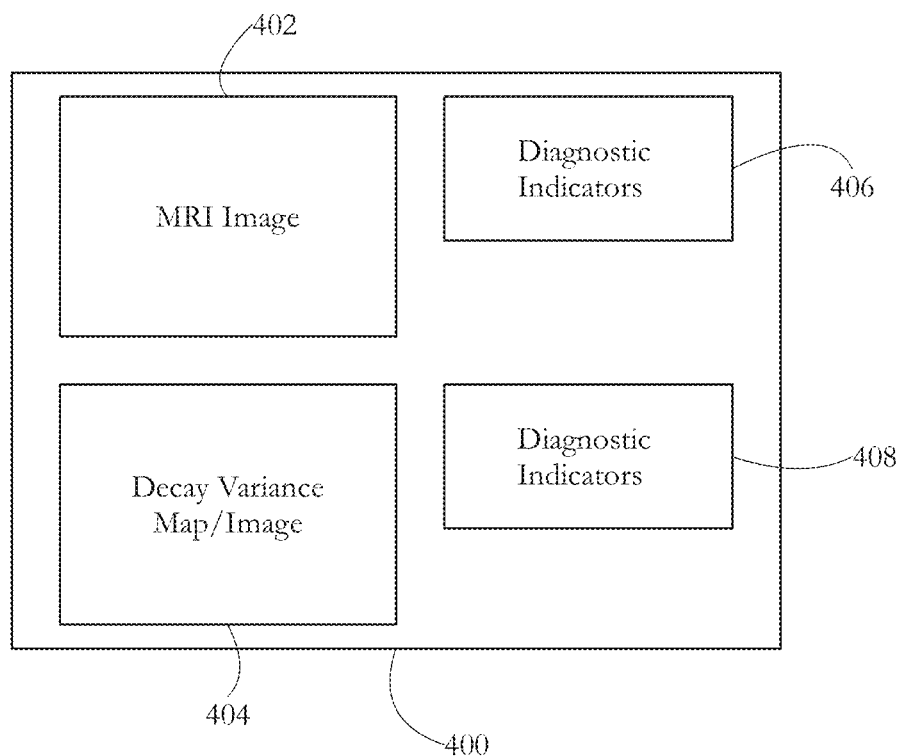
FIG. 4 illustrates an exemplary co-display of a magnetic resonance imaging (MRI) image, a corresponding decay variance map, and associated diagnostic indicators according to some embodiments of the present invention.

FIG. 4 shows an exemplary display 400 showing a report generated for medical practitioners and/or patients. Display 400 includes a number of components described below, which may be co-displayed in one window or displayed on different screens of a multi-screen sequence. Display 400 includes an MRI image 402, a corresponding decay variance map 404 displaying the same subject area as MRI image 402, and diagnostic indicator displays 406, 408 showing annotations, statistical and/or other diagnostic data characterizing the images 402, 404 and/or other patient data, and other data which may be useful to a clinical practitioner and/or patient. Diagnostic indicator displays 406, 408 may include scores computed for the image and/or parts thereof (e.g. each displayed disc), graphs representing signal sequences or statistical data, and other graphical representation of data generated by processing the underlying MRI data.

The following examples and discussion illustrate exemplary embodiments of the invention, and are not intended to limit the invention.

Example(s)

Intervertebral disc degeneration was assessed using decay variance maps as described above in rabbits, and correlated with histological grading. As part of a prior study, 25 New Zealand white rabbits underwent annular puncture to induce disc degeneration in 50 non-contiguous lumbar discs. At 16 weeks, the animals underwent multi-echo T2 MRI scanning and were euthanised. The discs were stained and examined histologically. Quantitative T2 relaxation maps were prepared using the non-linear least squares method. Decay variance maps were created by aggregating the deviation in the intensity of each echo signal from the expected intensity based on the previous rate of decay.

Decay variance maps showed a clear and well demarcated nucleus pulposus with a consistent rate of decay (low decay variance) in healthy discs that showed progressively more variable decay (higher decay variance) with increasing degeneration. Decay variance maps required significantly less time to generate (1.0±0.0 sec) compared with traditional T2 relaxometry maps (5 (±0.9) to 1788.9 (±116) seconds). Histology scores correlated strongly with decay variance scores ($r=0.82$, $p<0.01$), and weakly with T2 signal intensity ($r=0.32$, $p<0.01$) and Quantitative T2 Relaxometry ($r=0.39$, $p<0.01$). Decay variance had superior sensitivity and specificity for the detection of degenerate discs when compared to T2 signal intensity or quantitative T2 mapping.

The study results show that using multi-echo T2 MRI sequences, decay variance can quantitatively assess disc degeneration more accurately and with less image-processing time than quantitative T2 relaxometry in a rabbit disc puncture model. The technique may be used for quantitative assessment of disc degeneration on MRI scans in other mammalian subjects, including humans.

A number of new biological therapies are under active investigation in IVD degeneration including Growth and Differentiation Factor (GDF)-5, GDF-6, platelet-rich plasma, mesenchymal stem cells, tocilizumab and telomerase gene therapy. The gold standard for assessing both degeneration and regeneration of the IVD is histology, which requires the animal or sample to be sacrificed. The development of well-validated non-destructive techniques with acceptable accuracy in estimating overall health of the IVD is useful for assessing longitudinal changes in the IVD in routine clinical practice, and also for evaluating the efficacy of various biological therapies aimed at regenerating the IVD. Decay variance mapping as described above provides an option for non-destructive and objective assessment of IVD health.

Ideally, the result of such an assessments correlates well with the underlying disease processes, and is computationally efficient and practical to implement in routine clinical practice.

The extent of IVD degeneration, when visualized on a clinical MRI scan, is currently commonly described using qualitative grades, especially those described by Pfirmann et al. ("Magnetic Resonance Classification of Lumbar Intervertebral Disc Degeneration," Spine, Phila. Pa. 1976. 26 (2001)) and Thompson et al. ("Correlation of gross morphology and chemical composition with magnetic resonance images of human lumbar intervertebral discs," Trans. Orthop. Res. Soc. 13 (1988)).

More recently, a number of publications have described quantitative MRI in the research of degenerative disc disease, including work using T2* and T1-rho. See Ellingson et al., "Disc degeneration assessed by quantitative T2* (T2 star) correlated with functional lumbar mechanics," Spine (Phila. Pa. 1976). 38 (2013) E1533-E1540, and Paul et al., "Quantitative MRI in early intervertebral disc degeneration: T1rho correlates better than T2 and ADC with biomechanics, histology and matrix content," PLoS One, 13 (2018).

Ellingson et al. showed the predictive value of T2* quantitative relaxometry for sulphated glycosaminoglycans (S-GAG) content within intervertebral discs S-GAG content has been demonstrated to correlate with IVD degeneration and likely has a physiological role in the normal function of the IVD in maintaining osmotic pressure, as described by Roughley, "Biology of intervertebral disc aging and degeneration: involvement of the extracellular matrix," Spine (Phila. Pa. 1976). 29 (2004) 2691-2699.

Paul et al. demonstrated a strong correlation between T1-rho and IVD degeneration in a cadaveric caprine model. The IVDs were kept in culture for three weeks and exposed to different concentrations of chondroitinase for inducing degeneration. T1-rho is a difficult technique in that the estimation of molecular concentrations are susceptible to changes in temperature and pH, and this poses a significant challenge in its clinical implementation. See Owusu, "Characterization of T1rho sensitivity to metabolite and temperature changes," University of Iowa, 2015. https://ir.uiowa.edu/etd/1889/, and Chen, "Errors in quantitative T1rho imaging and the correction methods," Quant. Imaging Med. Surg. 5 (2015) 583-591.

The clinical use of quantitative imaging techniques using MRI data requires significant time, not only to acquire images but to also perform post-processing on the images. The required time and complexity pose monetary barriers to adoption. A review by The Association of University Radiologists' Radiology Research Alliance Quantitative Imaging Task Force found that there was "some antipathy among radiologist towards quantitative imaging" and that "with increasing emphasis on productivity, time spent performing quantitative imaging may be considered financially unrewarding" See Rosenkrantz et al., "Clinical utility of quantitative imaging," Acad. Radiol. 22 (2015) 33-49.

Other authors in the field of intervertebral disc degeneration have also acknowledged the need for improved non-destructive imaging techniques for the assessment of animal and preclinical models of disc degeneration. See e.g. Buckley, et al., "Critical aspects and challenges for intervertebral disc repair and regeneration—Harnessing advances in tissue engineering," JOR SPINE, 1 (2018) e1029, and Thorpe et al., "Leaping the hurdles in developing regenerative treatments for the intervertebral disc from preclinical to clinical," JOR SPINE, 1 (2018) e1027.

We hypothesized that the variability in the rate of signal decay over a multi-echo MRI sequence encodes information about the tissue states that could help distinguish between healthy and degenerate tissue, particularly in the context of IVD. We aimed to evaluate the difference between measured and expected signal decay for each echo in a multi-echo T2 MRI sequence, and correlate the results with histologically graded IVD degeneration in a rabbit IVD model.

Midline sagittal T2 weighted MRI data of 75 lumbar IVDs in 25 female New Zealand White Rabbits were collected as part of an earlier study, described by Miyazaki et al., "ISSLS PRIZE IN BASIC SCIENCE 2018: Growth differentiation factor-6 attenuated pro-inflammatory molecular changes in the rabbit anular-puncture model and degenerated disc-induced pain generation in the rat xenograft radiculopathy model," Eur. Spine J. Off. Publ. Eur. Spine Soc. Eur. Spinal Deform. Soc. Eur. Sect. Cerv. Spine Res. Soc. 27 (2018) 739-751. Degeneration was induced using 18 gauge needle-puncture in 50 IVDs, and the remaining 25 served as non-punctured controls. The degenerated IVDs were injected with either 10μl of PBS or 1, 10 or 100 μg of GDF-6.

Sixteen weeks following the needle-puncture (12 weeks after injection), the rabbits were euthanised, and sagittal multi-echo multi-spin T2 MRI was performed using a 7-Tesla BioSpec 70/30, (BRUKER, Billerica, Mass., USA). Unfixed samples were kept in a temperature controlled environment at 4-degree Celsius, not fixed in formalin, and were MRI scanned within 5 hours of euthanasia. Data were collected in DICOM (Digital Imaging and Communications in Medicine) file format. Thereafter, the rabbit IVDs were fixed and prepared for H+E staining, and the degree of disc degeneration was scored by a pathologist as described by Miyazaki et al. (supra).

All post-processing was performed using Matlab (v. R2017b, Mathworks Inc., Natick, USA). MRI data were analysed in three ways: firstly, the raw T2 weighted signal intensity data at the first echo time (13 ms) were examined; thereafter, quantitative T2 maps were created using pixel-wise curve fitting and non-linear least squares; and finally, decay variance maps were generated as described above with reference to eqs. (1-5).

Correction for the signal to noise ratio (which was taken to be inversely proportional to signal intensity at the first echo) was performed by dividing the decay variance by initial signal intensity on a pixel-wise basis.

All three maps (raw T2, quantitative T2, decay variance) were standardized by taking the $85^{th}$ percentile value as unity, and redistributing all pixel values between zero and one. Pixel values above the $85^{th}$ percentile were deemed to have a value of unity. All calculations were performed in Matlab, with 32 GB of accessible RAM and 8 Intel Core i7-7700K processor cores at 4.2 GHz. The processor time taken to generate each map for each technique was recorded using Matlab's inbuilt analytical tools.

Figure 5:
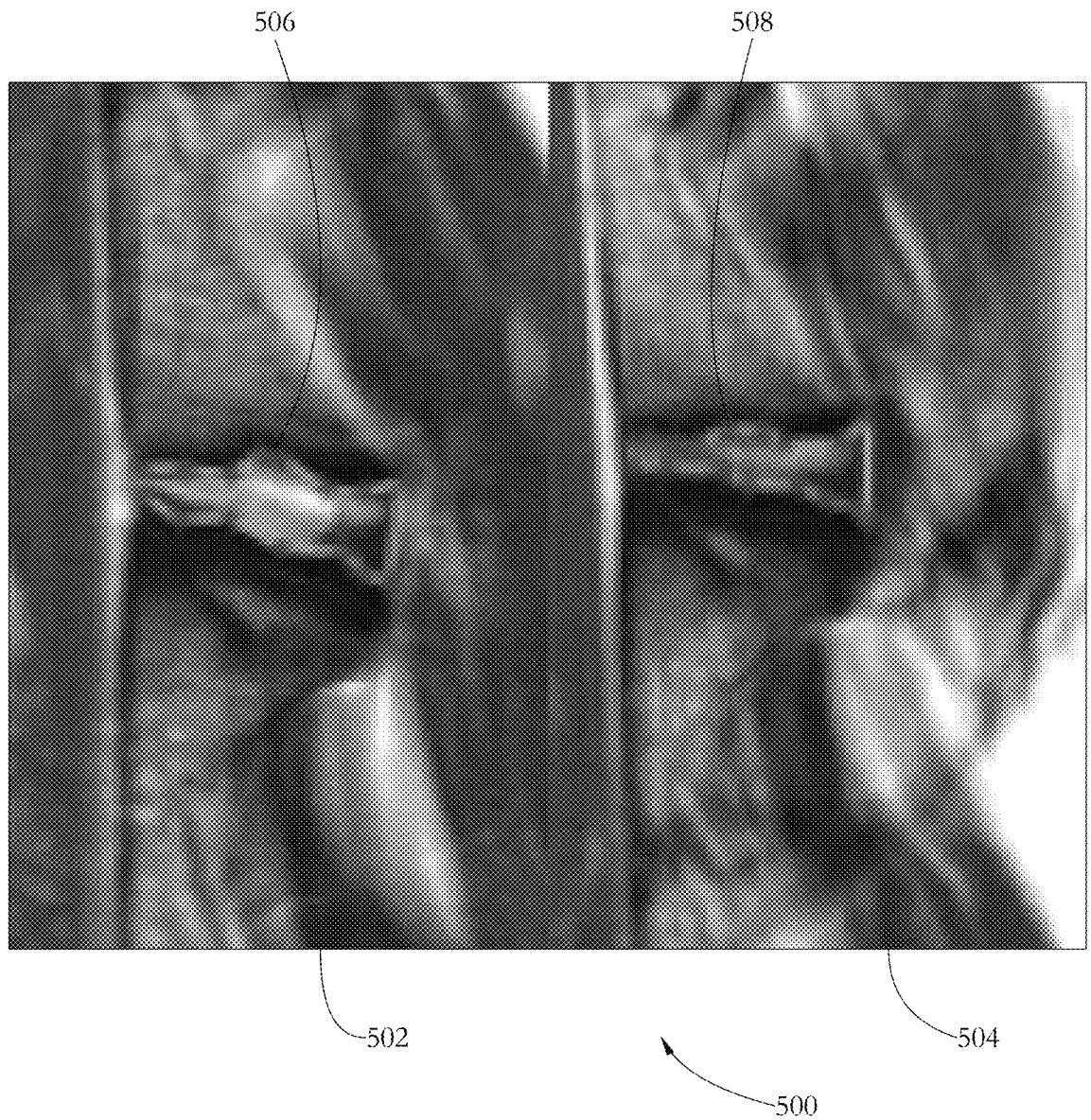
FIG. 5 illustrates images of a health and degenerate intervertebral disc (IVD) according to some embodiments of the present invention.

A region of interest (ROI) was selected including the entire NP and AF but excluding the EPs for each of the 75 IVDs, as shown generally at 500 in FIG. 5. The left panel 502 shows a healthy intervertebral disc while the right panel 504 shows a degenerate intervetebral disc in a rabbit lumbar spine. The representative ROIs 506, 508 were used for calculations of average quantitative T2 times, T2 weighted signal intensities, and decay variances for each disc. For validation purposes, ROIs were created twice by two observers at least one week apart.

Statistical analyses were performed using IBM SPSS software (v. 20, IBM, Armonk, USA), with the level of significance at 5% ($\alpha=0.01$). The primary objective was to investigate the extent to which each technique correlated with the histological grading for IVD degeneration. The distribution of IVD degeneration scores was both ordinal categorical and non-normally distributed, and therefore the non-parametric Spearman's rho test was used.

For each of the three techniques, sensitivities and specificities for the presence of IVD degeneration using predefined thresholds of 90% sensitivity (for specificity calculation) and 90% specificity (for sensitivity calculations) were calculated, and receiver operating characteristic (ROC) curves were generated.

Figure 6:
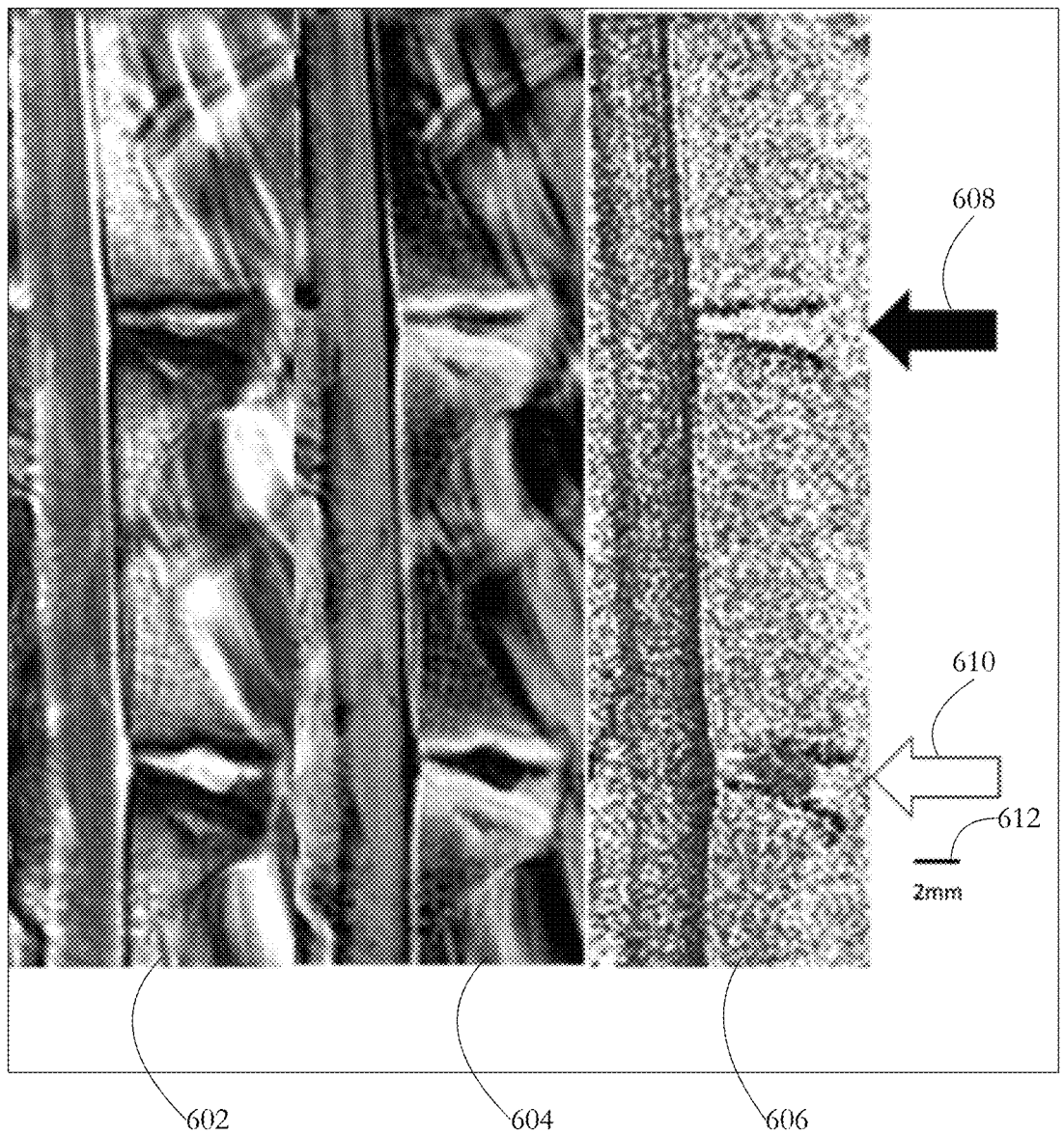
FIG. 6 illustrates three exemplary panels showing a T2-weighted image, an inverse of the T2-weighted image, and a decay variance map (image), respectively, of a same rabbit lumbar spine area according to some embodiments of the present invention.

FIG. 6 illustrates three exemplary panels 602, 604, 606 showing a T2-weighted image, an inverse of the T2-weighted image, and a decay variance map (image), respectively, of the same rabbit lumbar spine area. The cephalad IVD, indicated by the black arrow 608, had the best possible histology score (score 4), and caudal IVD, indicated by the arrow 610, had the worse possible histology score (score 12). The well-demarcated dark NP seen in healthy discs is almost absent in the lower disc. All windows were set programmatically between the $0^{th}$ and $70^{th}$ percentile values in order to facilitate a fair comparison between images representing different signals in different units. The scale bar 612 represents a distance of 2 mm.

As FIG. 6, decay variance mapping generated images that showed well-defined dark EP regions against a mid-grey vertebral body, and well-demarcated dark NP regions against a bright white AF in the healthy IVDs. With progressive IVD degeneration, the central dark NP became increasingly homogeneous with the AF.

FIG. 7 shows average scores for the segmented ROIs determined using the three MRI post-processing techniques for different IVD grades, alongside representative decay variance maps. As illustrated, the three MRI post-processing techniques all correlated with the histological scores for IVD degeneration (p<0.01).

Table 1 summarizes the strength of correlation between each MRI post-processing technique and the underlying histology score for intervertebral disc (IVD) degeneration. The average value in each disc area generated by each post-processing technique was correlated with the severity of IVD degeneration captured as described by Masuda et al. (supra). T2 signal intensity was weakly correlated (r=0.32, P<0.01) with histological grade of IVD degeneration. Quantitative T2 relaxometry was weakly correlated (r=0.39, P<0.01) with histological grade of IVD degeneration. Decay variance was strongly correlated (0.82) (P<0.01) with histological grade of IVD degeneration. While all the three techniques correlated positively and significantly with the histology scores, the strength of correlation was greatest for the decay variance technique.

TABLE 1

| Technique | Correlation Coefficient between Histological Grading of IVD and MRI Value | P value |
|---|---|---|
| T2 Weighted Signal Intensity | 0.32 | <0.01 |
| Quantitative T2 Relaxometry | 0.39 | <0.01 |
| Decay Variance | 0.82 | <0.01 |

Table 2A shows best possible specificities determined given a minimum value of sensitivity of 90% for the three techniques, while Table 2B shows best possible sensitivities determined given a minimum value of specificity of 90%. The data of Tables 2A-B were determined from 25 IVDs without degeneration (i.e. a histological IVD degeneration score of 4) and 50 IVDs with degeneration (i.e. a histological IVD degeneration score >5). Note that due to the ratio of 50 positive to 25 negative discs no cutoff has a specificity of 90%; the next incremental result was 92%.

TABLE 2A

| Technique | Sensitivity | Specificity |
|---|---|---|
| T2 Signal Intensity | 90% | 24% |
| Quantitative T2 | 90% | 52% |
| Decay Variance | 90% | 92% |

TABLE 2B

| Technique | Sensitivity | Specificity |
|---|---|---|
| T2 Signal Intensity | 32% | 92% |
| Quantitative T2 | 38% | 92% |
| Decay Variance | 92% | 92% |

Receiver Operating Characteristic (ROC) curves and tables were generated for every possible cutoff point for each of the three techniques. Complete sensitivity and specificity outcomes for every possible cut-off are shown as ROC curves in FIG. 8. The illustrated Receiver Operating Characteristic curves plot sensitivity vs. specificity for every possible cutoff point for each of the three techniques (T2 signal intensity at 13 ms, Quantitative T2 Relaxometry and decay variance) for 75 rabbit lumbar intervertebral discs (IVDs), 25 with no degeneration and 50 with degeneration induced by means of a needle puncture 16 weeks prior to magnetic resonance scanning. As shown, decay variance is superior at predicting the presence of IVD degeneration when compared with the other two techniques.

Table 3 illustrates a number of calculation times (mean±standard deviation) observed for various MRI analysis techniques in order to generate quantitative maps from MRI imaging data for rabbit lumbar spine images, including a decay variance technique as described above. Quantitative T2 maps were calculated using non-linear least squares in the Matlab curve fitting toolbox, the Levenberg Marquardt method using MRMap, and using a Maximum Likelihood Estimate method using Segment (a commercially available vendor independent post processing tool). Calculations were performed with 32 GB of accessible RAM and 8 Intel Core i7-7700K processor cores at 4.2 GHz.

TABLE 3

| Program | Method | Developer/Distributer | Calculation Time(seconds) |
|---|---|---|---|
| Matlab Curvefit Toolbox | Non-Linear Least Squares | Mathworks USA | 1788.8 (± 116.0) |
| MR Map | Levenberg-Marquardt | Deutsches Herzzentrum Berlin, German | 37.3 (± 3.5) |
| Segment | Maximum Likelihood Estimate | Lund Cardiac MM Group/Medvisio Ab | 5.0 (+ 0.9) |
| Decay Variance | Decay Variance | Authors of the present study | 1.0 (± 0.0) |

The calculation time for the decay variance maps was less than 0.1% of the calculation time for the conventional quantitative T2 maps by curve fitting. The average calculation time for quantitative T2 maps was 1788.9 [+/−115.98] seconds and that for the Decay Variance maps was 1.02 seconds (+/−0.03).

The exemplary study described above assessed a new post-processing tool for multi-echo MRI scans that showed an excellent correlation with degenerative changes as quantified by histological grading in a rabbit lumbar IVD degeneration model. Decay variance was able to separate degenerate from non-degenerate IVDs more reliably than quantitative T2 relaxometry or T2 signal intensity at 13 ms.

The calculation of quantitative T2 maps by non-linear least squares methods assumes a single underlying exponential decay curve with a constant rate of signal decay. See Cheng et al., "Practical medical applications of quantitative MR relaxometry," J. Magn. Reson. Imaging. 36 (2012) 805-824. The constant-decay assumption implies that each pixel contains only a single substance, which is valid only when performing an MRI on a chemically pure sample but may be invalid when applied to a biological material. Further, T1 relaxation cannot be switched off and will contribute to signal decay in the calculation of T2 relaxation times.

Reasonable acquisition times in living subjects limit the spatial resolution of MRI. The MRI scans in the example described above were acquired on a 7T scanner with a pixel (voxel) width of 180 micrometres. While this is a much finer spatial resolution than is generally available in clinical practice, it is a large area in histological terms.

Figure 9:
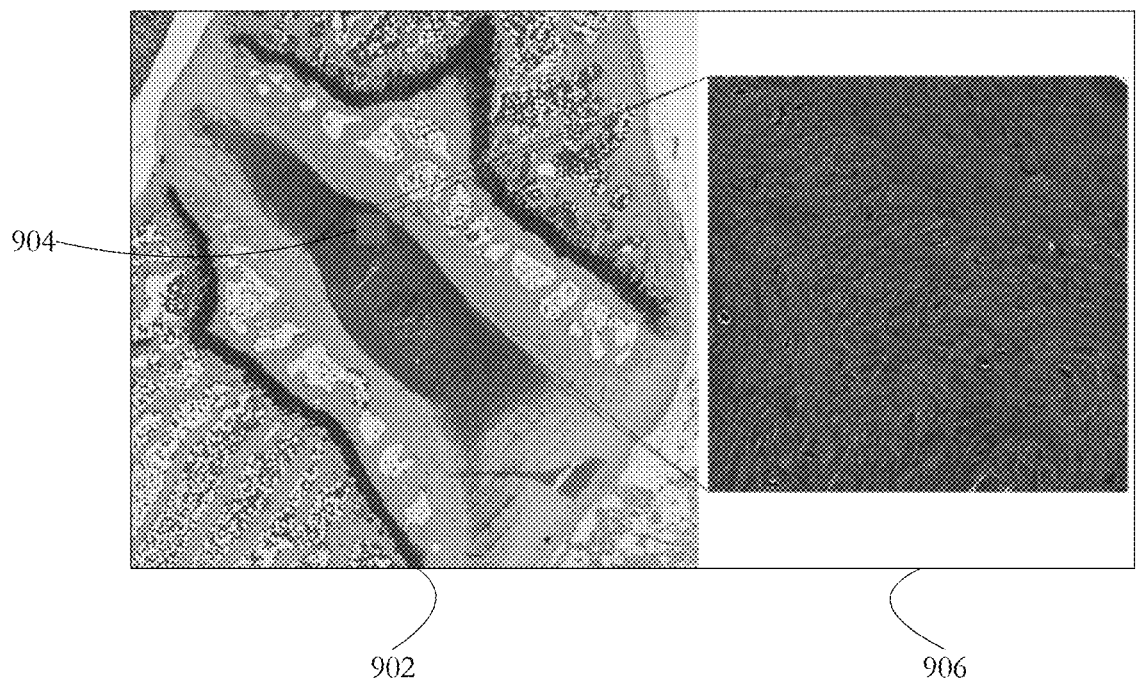
FIG. 9 shows a stained nucleus pulposus (NP) of a degenerate intervertebral disc and a detail of a highlighted area, according to some embodiments of the present invention.

FIG. 9 shows a Safranin 0-stained nucleus pulposus of a degenerate intervertebral disc in a left-panel 902. A micrograph in a right panel 906 shows in detail an area 904 of the left panel. The entirety of the contents of micrograph 906 would fall within one pixel of a magnetic resonance image (180×180 μm).

Figure 8:
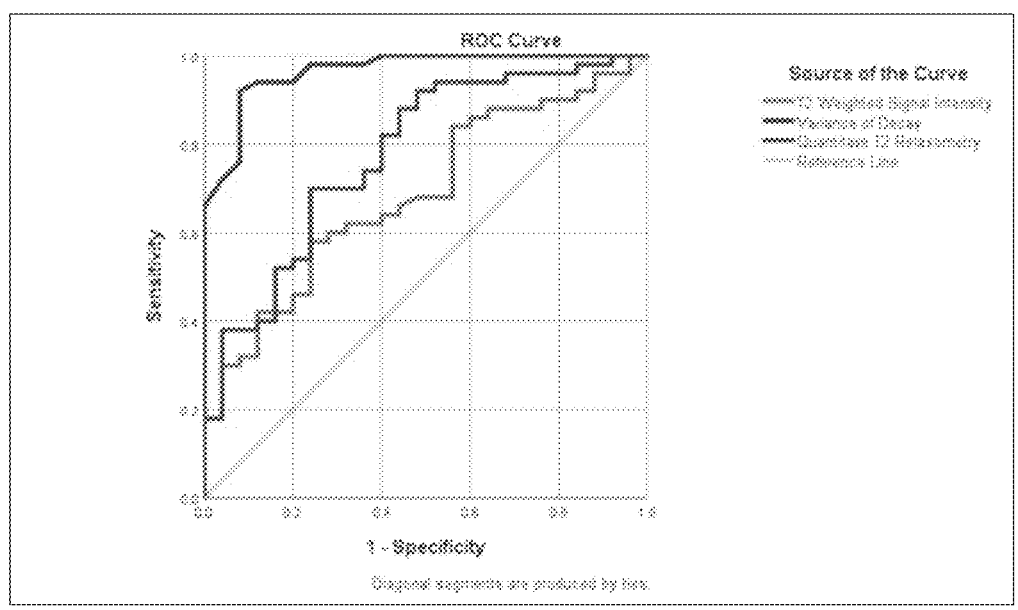
FIG. 8 shows exemplary receiver operating characteristic (ROC) curves illustrating an exemplary interplay/tradeoff between test sensitivity and specificity according to some embodiments of the present invention.

The underlying decay curve for one pixel (e.g. voxel) of a biological material, which likely contains a mixture of various cell types, proteins, lipids, water and other molecules, is more likely to be a superposition of multiple discrete and varied decay curves of different weight (illustrated in FIG. 8). Thus, the degree to which the observed decay in signal intensity over time in a given pixel varies from a pure decay curve provides information, as a surrogate marker, for the bio-magnetic heterogeneity within the given pixel.

Calculation of quantitative T2 maps by conventional methods is computationally intensive as it requires a curve fitting operation for each pixel. See Cheng et al, supra. Calculation of a decay variance map, by comparison, may be achieved in some embodiments by simple addition, subtraction and division, and may be therefore orders of magnitude less computationally intensive. Calculation of decay variance maps need not require special preparation or alteration to MRI image acquisition, and can be applied retrospectively to multi-echo T2 weighted sequences generated by conventional devices.

Low back pain is a condition afflicting 80% of adults in their lifetime, but the ability to identify causes on MRI using ordinal grading scales for IVD degeneration, such as described by Pfirrmann et al., is limited. In a study of 284 participants with low back pain, the authors reported no correlation between IVD degeneration quantified using Pfirrmann grades and pain or disability on standardised testing instruments, including the Roland-Morris Disability Index, the Oswestry Disability Index and The Short Form (SF)-12 questionnaires. See Corniola et al., "Correlation of pain, functional impairment, and health-related quality of life with radiological grading scales of lumbar degenerative disc disease," Acta Neurochir. (Wien). 158 (2016) 499-505.

In addition to potential intrinsic biological differences between humans and rabbits, this animal model may differ from human IVD degeneration in that most cases of IVD degeneration in the present rabbit model are severe. Most discs were either entirely intact or very severely degenerate (degeneration scores of 11 or 12 out of 12), with relatively few cases of mild or moderate IVD degeneration.

The techniques described above may be applied to and validated in T2* weighted multi-echo imaging or other types of MRI images. Decay variance may also be tested in other tissues. Repeat measurements may be performed over time for a patient in order to assess change in decay variance over time.

The results above show that decay variance is a novel and computationally efficient technique, which has a stronger correlation with histological defined severity of IVD degeneration than quantitative T2 weighted imaging. Confirmation of the observed correlation with histological changes observed in the present study would encourage implementation of this technique in clinical practice in order to allow for objective and accurate assessment of IVD health.

It will be clear to one skilled in the art that the above embodiments may be altered in many ways without departing from the scope of the invention. For example, post-processing as described herein may be implemented in one or more programming languages such as C or C++. Different components of exemplary described client-server systems may be implemented using different programming languages and/or technology environments. In some embodiments, methods as described herein may be used to generate images and related data for mammalian and/or other animal subjects including rabbits, humans, and other species. Accordingly, the scope of the invention should be determined by the following claims and their legal equivalents.

What is claimed is:

1. A method comprising employing a computer system including at least one processor to:

determine a signal decay variance for a pixel or pixel subset of a plurality of pixels of at least one magnetic resonance imaging (MRI) image of at least one region of interest of a subject, the signal decay variance representing a time-variance of a decay rate of an MRI signal characterizing the pixel or pixel subset;

generate an MRI signal decay variance map of the at least one region of interest according to determined signal decay variances characterizing the at least one MRI image; and generate a tissue degeneration indicator for the subject according to the MRI signal decay variance map.

2. The method of claim 1, wherein the MRI signal is a T2 signal.

3. The method of claim 1, wherein determining the signal decay variance comprises determining a sequence of signal retention ratios, each signal retention ratio representing a ratio between consecutive signal intensities within the MRI signal.

4. The method of claim 3, wherein determining the signal decay variance comprises a determining a sequence of differences between consecutive signal retention ratios.

5. The method of claim 3, wherein determining the signal decay variance comprises determining a sum of differences between consecutive signal retention ratios over a timespan of the MRI signal.

6. The method of claim 1, wherein determining the signal decay variance comprises normalizing a raw signal decay variance according to an initial signal intensity of the MRI signal.

7. The method of claim 1, further comprising employing the computer system to identify a plurality of regions of interest within the at least one MRI image, wherein the tissue degeneration indicator is generated according to MRI signal decay variance maps for the plurality of regions of interest.

8. The method of claim 1, wherein the at least one region of interest comprises at least part of the subject's spine, and wherein the tissue degeneration indicator characterizes a degeneration of intervertebral discs of the subject.

9. The method of claim 8, wherein the at least one region of interest comprises nucleus pulposus (NP) and annulus fibrosus (AF) areas, and excludes cartilaginous endplate (EP) areas of the subject.

10. The method of claim 1, wherein the at least one region of interest comprises at least part of a joint of the subject, and wherein the tissue degeneration indicator characterizes a degeneration of the joint.

11. The method of claim 1, wherein the subject is a human subject.

12. A non-transitory computer-readable medium encoding instructions which, when executed by a computer system cause the computer system to:
   determine a signal decay variance for a pixel or pixel subset of a plurality of pixels of at least one magnetic resonance imaging (MRI) image of at least one region of interest of a subject, the signal decay variance representing a time-variance of a decay rate of an MRI signal characterizing the pixel or pixel subset;
   generate an MRI signal decay variance map of the at least one region of interest according to determined signal decay variances characterizing the at least one MRI image; and
   generate a tissue degeneration indicator for the subject according to the MRI signal decay variance map.

13. The computer-readable medium of claim 12, wherein the MRI signal is a T2 signal.

14. The computer-readable medium of claim 12, wherein determining the signal decay variance comprises determining a sequence of signal retention ratios, each signal retention ratio representing a ratio between consecutive signal intensities within the MRI signal.

15. The computer-readable medium of claim 14, wherein determining the signal decay variance comprises a determining a sequence of differences between consecutive signal retention ratios.

16. The computer-readable medium of claim 14, wherein determining the signal decay variance comprises determining a sum of differences between consecutive signal retention ratios over a timespan of the MRI signal.

17. The computer-readable medium of claim 12, wherein determining the signal decay variance comprises normalizing a raw signal decay variance according to an initial signal intensity of the MRI signal.

18. The computer-readable medium of claim 12, wherein the instructions further cause the computer system to identify a plurality of regions of interest within the MRI image, wherein the tissue degeneration indicator is generated according to MRI signal decay variance maps for the plurality of regions of interest.

19. The computer-readable medium of claim 12, wherein the at least one region of interest comprises at least part of the subject's spine, and wherein the tissue degeneration indicator characterizes a degeneration of intervertebral discs of the subject.

20. The computer-readable medium of claim 19, wherein the at least one region of interest comprises nucleus pulposus (NP) and annulus fibrosus (AF) areas, and excludes cartilaginous endplate (EP) areas of the subject.

21. The computer-readable medium of claim 12, wherein the at least one region of interest comprises at least part of a joint of the subject, and wherein the tissue degeneration indicator characterizes a degeneration of the joint.

22. The computer-readable medium of claim 12, wherein the subject is a human subject.

23. An apparatus comprising at least one processor programmed to:
   determine a signal decay variance for a pixel or pixel subset of a plurality of pixels of at least one magnetic resonance imaging (MRI) image of at least one region of interest of a subject, the signal decay variance representing a time-variance of a decay rate of an MRI signal characterizing the pixel or pixel subset;
   generate an MRI signal decay variance map of the at least one region of interest according to determined signal decay variances characterizing the at least one MRI image; and
   generate a tissue degeneration indicator for the subject according to the MRI signal decay variance map.

24. The apparatus of claim 23, further comprising an MRI scanner configured to take the MRI image.

* * * * *